US012697063B2

(12) United States Patent
Farmer

(10) Patent No.: US 12,697,063 B2
(45) Date of Patent: Aug. 4, 2026

(54) SYSTEM AND METHOD FOR PROVIDING FOUR RING VISUAL ELECTROPHYSIOLOGY STIMULUS

(71) Applicant: Diagnosys LLC, Lowell, MA (US)

(72) Inventor: Jeffrey D. Farmer, Chelmsford, MA (US)

(73) Assignee: Diagnosys LLC, Lowell, MA (US)

( * ) Notice: Subject to any disclaimer, the term of this patent is extended or adjusted under 35 U.S.C. 154(b) by 771 days.

(21) Appl. No.: 17/473,144

(22) Filed: Sep. 13, 2021

(65) Prior Publication Data

US 2022/0079503 A1 Mar. 17, 2022

Related U.S. Application Data

(60) Provisional application No. 63/077,328, filed on Sep. 11, 2020.

(51) Int. Cl.
| | |
|---|---|
| *A61B 5/398* | (2021.01) |
| *A61B 3/10* | (2006.01) |
| *A61B 5/00* | (2006.01) |
| *A61B 5/297* | (2021.01) |

(52) U.S. Cl.
CPC ............... *A61B 5/398* (2021.01); *A61B 3/10* (2013.01); *A61B 5/297* (2021.01); *A61B 5/4848* (2013.01); *A61B 5/7225* (2013.01); *A61B 2560/02* (2013.01)

(58) Field of Classification Search
CPC ........... A61B 5/398; A61B 3/10; A61B 5/297; A61B 5/4848; A61B 5/7225; A61B 2560/02

USPC ......................................................... 600/558
See application file for complete search history.

(56) References Cited

U.S. PATENT DOCUMENTS

| | | | | |
|---|---|---|---|---|
| 3,574,450 A | * | 4/1971 | White .................... | A61B 5/378 |
| | | | | 351/239 |
| 5,632,282 A | * | 5/1997 | Hay ........................ | G16H 15/00 |
| | | | | 600/558 |
| 6,315,412 B1 | * | 11/2001 | Snodderly .............. | A61B 3/063 |
| | | | | 351/200 |

(Continued)

FOREIGN PATENT DOCUMENTS

| | | | | |
|---|---|---|---|---|
| WO | WO-2006106548 A1 | * | 10/2006 | ............. A61B 5/398 |
| WO | WO-2020121276 A1 | * | 6/2020 | ............... A61B 3/10 |

OTHER PUBLICATIONS

Moschos, M.M., Triglianos, A., Rotsos, T. et al. Tilted disc syndrome: an OCT and mfERG study. Doc Ophthalmol 119, 23-28 (2009). https://doi.org/10.1007/s10633-009-9165-x (Year: 2009).*

(Continued)

*Primary Examiner* — Jacqueline Cheng
*Assistant Examiner* — Jonathan E. Cooper
(74) *Attorney, Agent, or Firm* — Pandiscio & Pandiscio

(57) ABSTRACT

A system for testing different regions of the retina of a subject for retinal function, said system comprising: a monitor configured to display a visual electrophysiology stimulus to the subject, wherein the visual electrophysiology stimulus comprises a four ring visual electrophysiology stimulus; at least one active electrode; at least one reference electrode; and a computer configured to receive electrical signals from said at least one active electrode and said at least one reference electrode, and process the electrical signals.

32 Claims, 8 Drawing Sheets

(56) References Cited

U.S. PATENT DOCUMENTS

| | | | | |
|---|---|---|---|---|
| 8,684,946 B1* | 4/2014 | Sims | .................... | A61B 3/0008 |
| | | | | 351/246 |
| 2007/0091265 A1* | 4/2007 | Kardon | .................... | A61B 3/12 |
| | | | | 351/206 |
| 2009/0231545 A1* | 9/2009 | Peyman | ............... | A61B 3/0091 |
| | | | | 351/246 |
| 2010/0091242 A1* | 4/2010 | Baglini | ............... | A61B 5/7228 |
| | | | | 351/205 |
| 2012/0277622 A1* | 11/2012 | Regini | .................. | A61B 5/398 |
| | | | | 600/558 |
| 2020/0093362 A1* | 3/2020 | Jackson | ............... | A61B 3/0008 |
| 2022/0031503 A1* | 2/2022 | Dorin | .................... | A61F 9/008 |

OTHER PUBLICATIONS

Hood et al., ISCEV standard for clinical multifocal electroretinography (mfERG) (2011 edition), Doc. Ophthalmol, vol. 124, Oct. 31, 2011, pp. 1-13.
Browning et al., Relative sensitivity and specificity of 10-2 visual fields, multifocal electroretinography, and spectral domain optical coherence tomography in detecting hydroxychloroquine and chloroquine retinopathy, Clinical Ophthalmology, vol. 8, Jul. 25, 2014, pp. 1389-1399.

* cited by examiner

ISCEV standard 61
hexagon stimulus

ISCEV standard 103
hexagon stimulus

Note: 30 degree field of view radius (outer circle), 20 degree (middle circle) and 10 degree (inner circle) shown on standard ISCEV mfERG stimuli Test Example 1 - Test Report and analysis of ERG recordings using the 4-ring stimulus Amplitude and Ratios of Ring Amplitudes:

Right eye:

| Ring | P1 amplitude (uVolt/deg*2) | Ring Ratio |
|------|----------------------------|------------|
| 1 | 78.0 | |
| 2 | 40.7 | |
| 3 | 17.0 | |
| 4 | 7.9 | |
| 2 / 4 | | 5.2x |
| 3 / 4 | | 2.2x |

Left eye:

| Ring | P1 amplitude (uVolt/deg*2) | Ring Ratio |
|------|----------------------------|------------|
| 1 | 77.4 | |
| 2 | 37.8 | |
| 3 | 14.6 | |
| 4 | 7.0 | |
| 2 / 4 | | 5.4x |
| 3 / 4 | | 2.1x | diagnosys

Test Example 2 – Test Report and analysis of ERG recordings using the 4-ring stimulus Amplitude and Ratios of Ring Amplitudes:

Right eye:

| Ring | P1 amplitude (uVolt/deg*2) | Ring Ratio |
|------|----------------------------|------------|
| 1 | 79.0 | |
| 2 | 45.2 | |
| 3 | 17.0 | |
| 4 | 8.1 | |
| 2/4 | | 5.6x |
| 3/4 | | 2.1x |

Left eye:

| Ring | P1 amplitude (uVolt/deg*2) | Ring Ratio |
|------|----------------------------|------------|
| 1 | 83.9 | |
| 2 | 38.2 | |
| 3 | 14.5 | |
| 4 | 6.9 | |
| 2/4 | | 5.5x |
| 3/4 | | 2.1x |

SYSTEM AND METHOD FOR PROVIDING FOUR RING VISUAL ELECTROPHYSIOLOGY STIMULUS

REFERENCE TO PENDING PRIOR PATENT APPLICATIONS

This patent application claims benefit of pending prior U.S. Provisional Patent Application Ser. No. 63/077,328, filed Sep. 11, 1920 by Diagnosys LLC and Jeffrey D. Farmer for FOUR RING VISUAL ELECTROPHYSIOLOGY STIMULUS (Attorney's Docket No. DIAGNOSYS-12 PROV), which patent application is hereby incorporated herein by reference.

FIELD OF THE INVENTION

This invention relates to systems and methods for providing visual electrophysiology stimulus in general, and more particularly to a novel four ring visual electrophysiology stimulus for providing visual electrophysiology.

BACKGROUND OF THE INVENTION

Diagnosys LLC of Lowell, Mass., USA is a medical device company that manufactures ophthalmic electrophysiology equipment. Such ophthalmic electrophysiology equipment typically stimulates the eye (i.e., the retina) using flashes of light and/or moving patterns of light, and measures the resulting electrical response to the stimulus of the eye using (i) electrodes applied onto the surface of the eye or on skin near the eye (i.e., in order to obtain an electroretinogram, "ERG"), or (ii) electrodes applied to the scalp above the visual cortex (i.e., in order to obtain a visual evoked potential, "VEP"). Ophthalmic electrophysiology is considered to be the only objective measure of visual function; all other ophthalmic diagnostics are either subjective, or a measure of anatomical structure (rather than a measure of ophthalmic function).

Hydroxychloroquine (HCQ) and its predecessor, chloroquine (CQ), are antimalarial drugs with well-established benefits for treating rheumatoid arthritis, lupus and other connective tissue and skin disorders. HCQ and/or CQ have been used in some instances to treat patients suffering from COVID-19, although to date such usage to treat COVID-19 is typically a relatively short-term usage. Extensive research has shown that long-term usage of either drug (i.e., HCQ and/or CQ) is associated with retinal toxicity. Therefore, early detection of HCQ/CQ retinopathy is imperative to minimize the risk of any vision loss that may occur as a result of such retinopathy.

The American Academy of Ophthalmology (AAO) recommends the use of objective testing to screen for retinal toxicity in patients taking HCQ and/or CQ, as well as for retinal toxicity that may be associated with other drugs that are known to cause similar retinal toxicities.

In brief, electroretinography operates so as to provide an objective examination of retinal function in a patient by stimulating the eye (e.g., using light), and then measuring and analyzing the electrical response of the eye to the stimulus (e.g., using one or more electrodes and a computer configured to analyze the electrical signals received by the one or more electrodes).

One type of electroretinography test is multifocal electroretinography (mfERG), which may be used to provide objective examination of retinal function in patients taking HCQ and/or CQ, as well as for retinal toxicity that may be associated with other drugs that are known to cause retinal toxicities.

Another objective test that may be performed to screen for retinal toxicity in a subject is spectral domain optical coherence tomography (sdOCT), which analyzes images of the retinal layers to detect retinal toxicity.

A 2019 study suggests that although spectral domain optical coherence tomography (sdOCT) can detect retinal toxicity, mfERG is more sensitive to retinal dysfunction that may occur before structural abnormalities appear. Also, mfERG can be useful in confirming the absence of retinal toxicity when perimetry (i.e., the measurement of a person's field of vision) or other tests detect abnormalities. In addition, while most retinal toxicity research has focused on HCQ/CQ drugs, an increasing number of clinical cases suggest other medications may also contribute to similar vision loss. Vision loss from toxicity caused by these types of drugs tends to happen in ring regions centered around the fovea of the retina.

Stimuli for performing visual electrophysiology have been used for many years. FIG. 1 shows the two standard stimuli typically used for performing visual electrophysiology, i.e., the 61-hexagon stimulus and the 103-hexagon stimulus. In each case, these stimuli were designed for general ERG tests of the retina. Such stimuli have also been used in mfERG tests to detect toxicity, but neither are optimal for the purpose of toxicity detection and monitoring. The primary deficiencies of these two stimuli for toxicity monitoring are that neither stimulus directly stimulate the area of the retina where toxicity occurs, and both stimuli take a longer period of time to run on a subject than is typically desired. In typical clinical use, the 61-hexagon stimulus is run for at least 4 minutes on the subject, and the 103-hexagon stimulus is run for at least 8 minutes on the subject.

Thus, there is a need for a new and improved system and method for providing a visual electrophysiology stimulus which directly stimulates the area of the retina where toxicity most likely will occur, and which is faster to perform on a subject than existing visual electrophysiology systems.

SUMMARY OF THE INVENTION

The present invention comprises the provision and use of a new and improved system for providing a visual electrophysiology stimulus.

In one preferred form of the invention, there is provided a system for testing different regions of the retina of a subject for retinal function, said system comprising:

a monitor configured to display a visual electrophysiology stimulus to the subject, wherein the visual electrophysiology stimulus comprises a four ring visual electrophysiology stimulus;

at least one active electrode;

at least one reference electrode; and a computer configured to receive electrical signals from said at least one active electrode and said at least one reference electrode, and process the electrical signals.

In another preferred form of the invention, there is provided a method for testing different regions of the retina of a subject for retinal function, said method comprising:

providing a system comprising:

a monitor configured to display a visual electrophysiology stimulus to the subject, wherein the visual electrophysiology stimulus comprises a four ring visual electrophysiology stimulus;

at least one active electrode;

at least one reference electrode; and a computer configured to receive electrical signals from said at least one active electrode and said at least one reference electrode, and process those electrical signals;

attaching said at least one active electrode to the subject;

attaching said at least one reference electrode to the subject;

using said monitor to display said four ring visual electrophysiology stimulus to stimulate the eye of the subject; and using said computer to receive electrical signals from said at least one active electrode and said at least one reference electrode, and process the electrical signals.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 7 and 8 are schematic views showing an exemplary test report produced by the novel visual electrophysiology system of the present invention.

DETAILED DESCRIPTION OF THE PREFERRED EMBODIMENTS

The present invention comprises the provision and use of a new and improved system for providing an electrophysiology stimulus.

Figure 2:
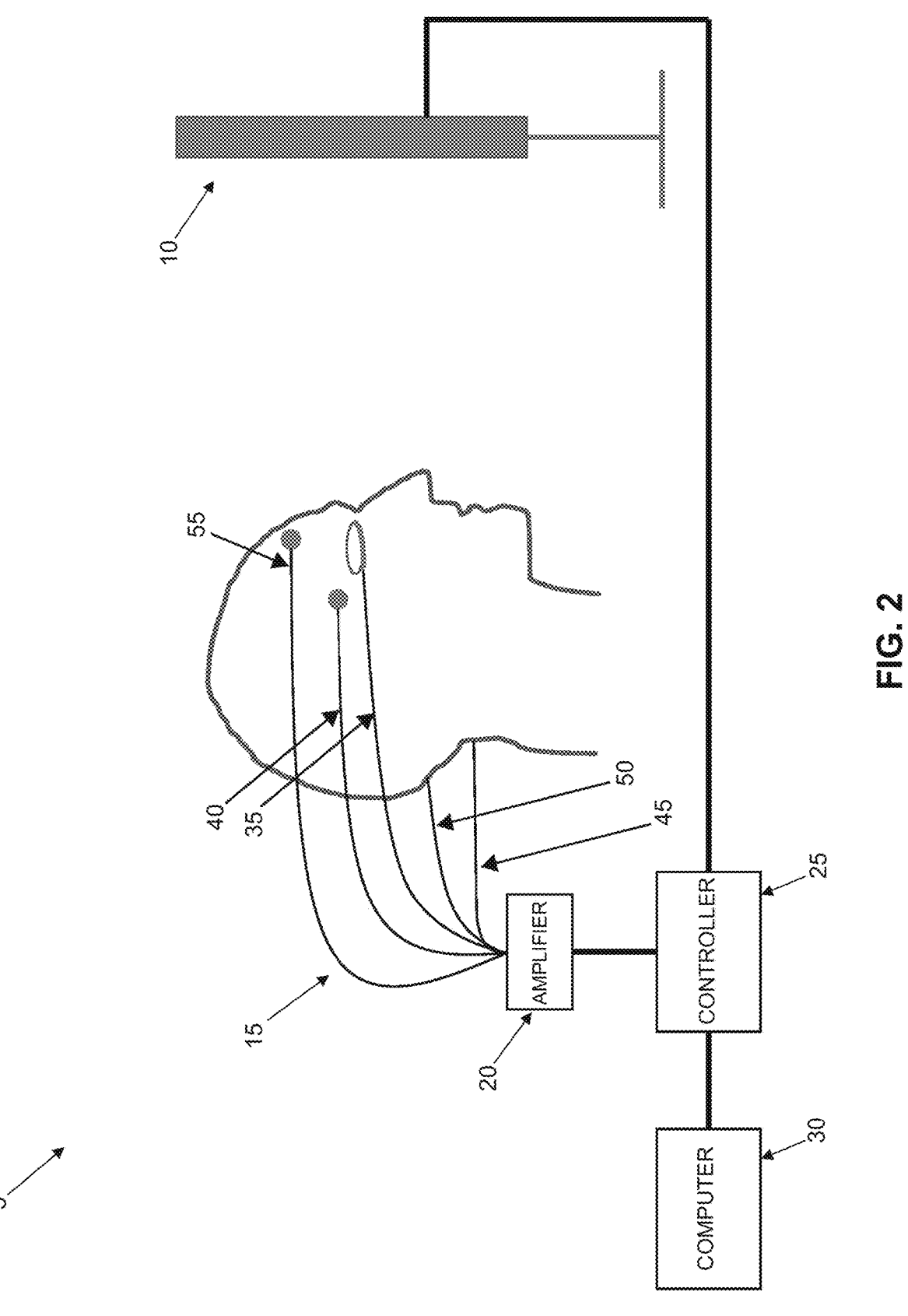
FIG. 2 is a schematic view showing a novel visual electrophysiology system formed in accordance with the present invention.

More particularly, and looking now at FIG. 2, the present invention comprises a visual electrophysiology system 5. Visual electrophysiology system 5 generally comprises a display 10 for displaying a visual stimulus to the eye(s) of a subject, a cluster of electrodes 15 for detecting electrical signals in the eye(s) of the subject, an amplifier 20 for amplifying electrical signals detected by cluster of electrodes 15, a controller 25 for controlling display 10 and/or cluster of electrodes 15 through amplifier 20, and a computer 30 for providing programming to controller 25 and/or for receiving and/or processing electrical signals detected by cluster of electrodes 15.

In one preferred form of the present invention, cluster of electrodes 15 comprises a right-eye active electrode 35, a right-eye reference electrode 40, a left-eye active electrode 45, a left-eye reference electrode 50 and a ground electrode 55.

Figure 3:
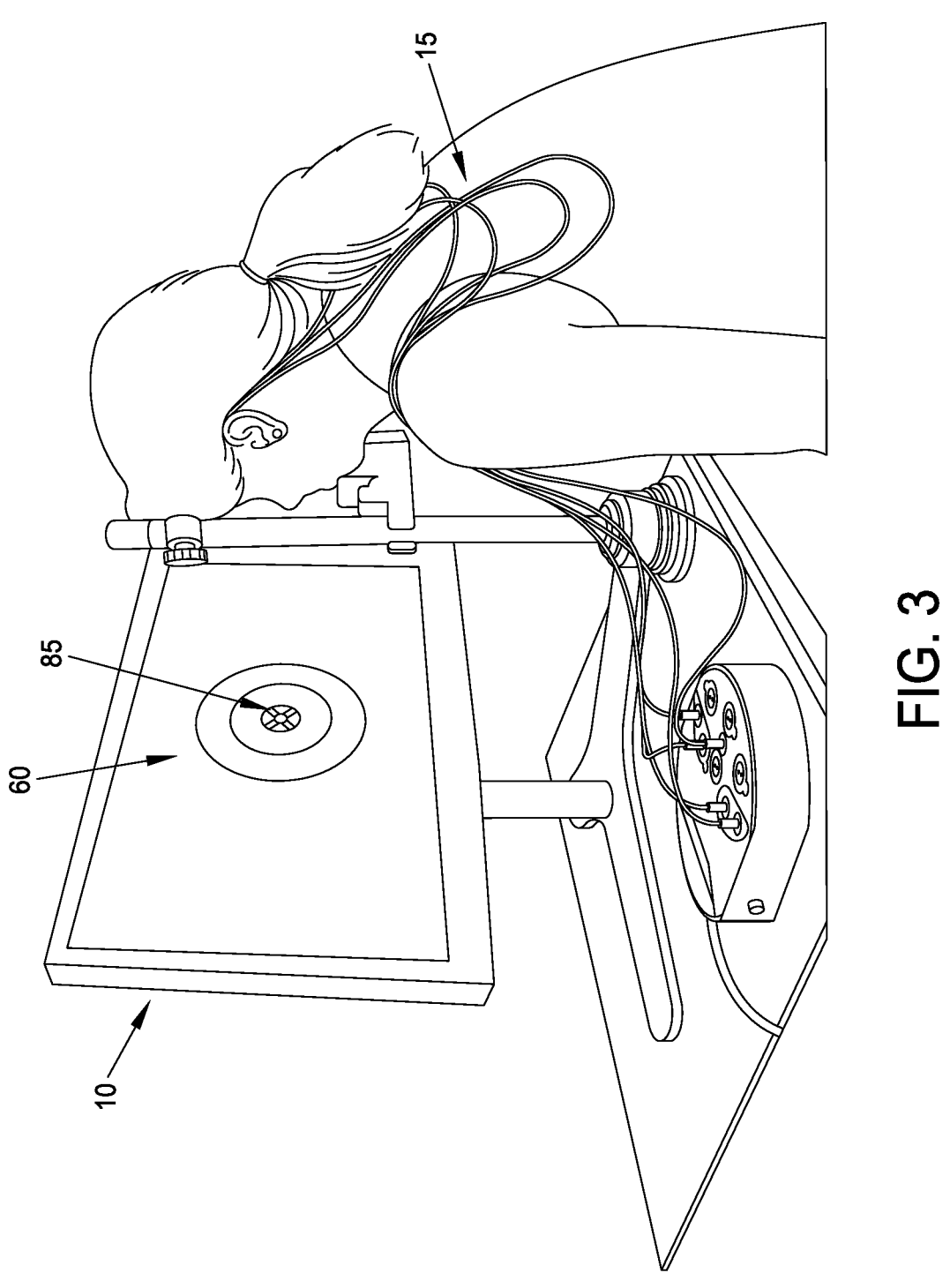
FIGS. 3-5 are schematic views showing novel electrophysiology stimulus formed in accordance with the present invention.

Display 10 is preferably a monitor (e.g., an LCD monitor, an OLED monitor, a CRT monitor etc.). Display 10 is configured to emit a novel four ring visual electrophysiology stimulus (FRVES) 60 (FIG. 3). FRVES 60 is a visual stimulus specifically designed to stimulate a preferred portion of a retina of a primate subject (e.g., human, monkey, etc.), whereby to determine if the subject's retina has lost some or all of its function due to drug toxicity. More particularly, FRVES 60 is designed to stimulate, specifically, the parafovea and perifovea regions of the macula, individually, and to stimulate a third region of the retina as a reference, as will hereinafter be discussed in further detail.

Figure 4:
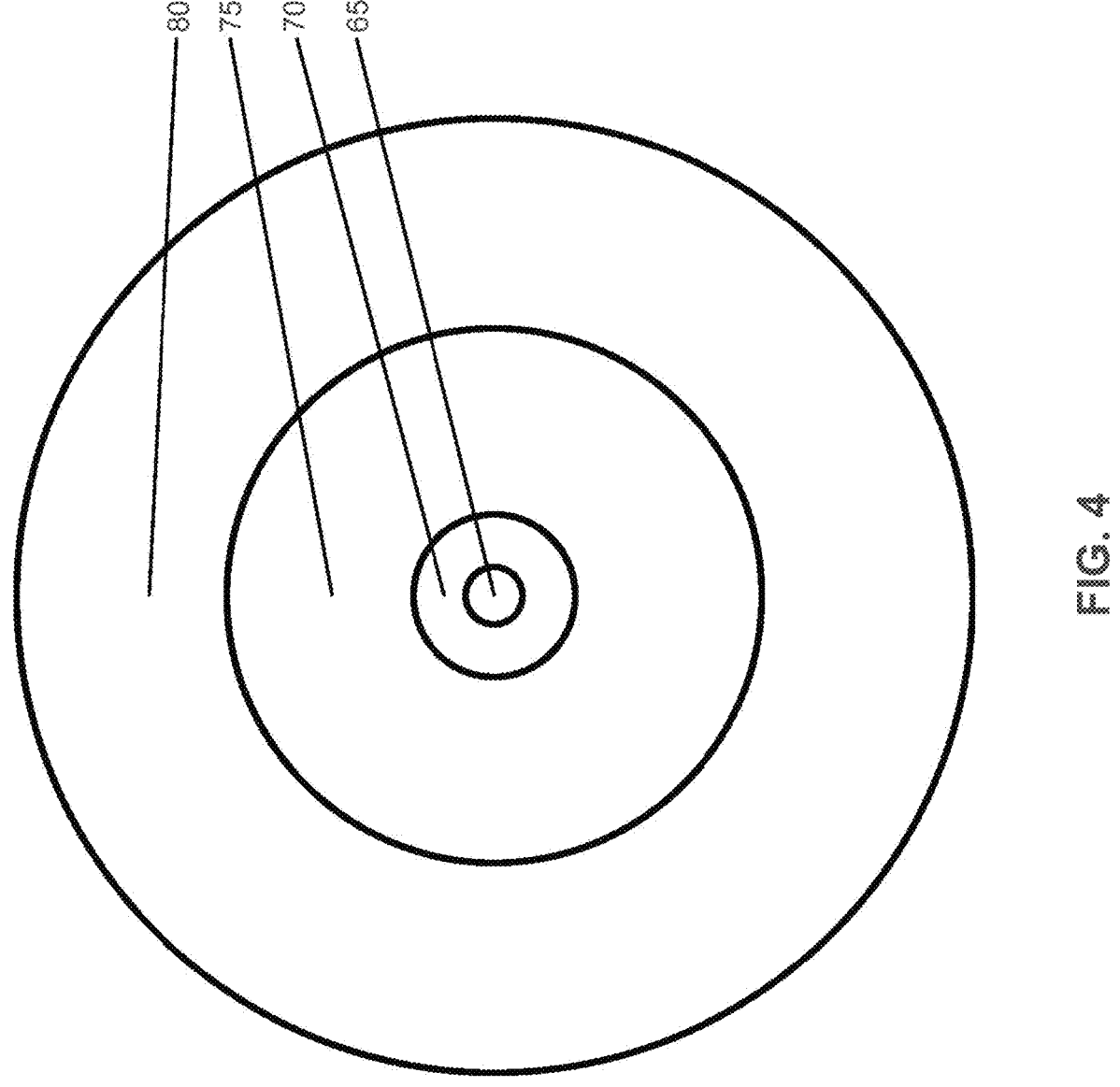
Figure 5:
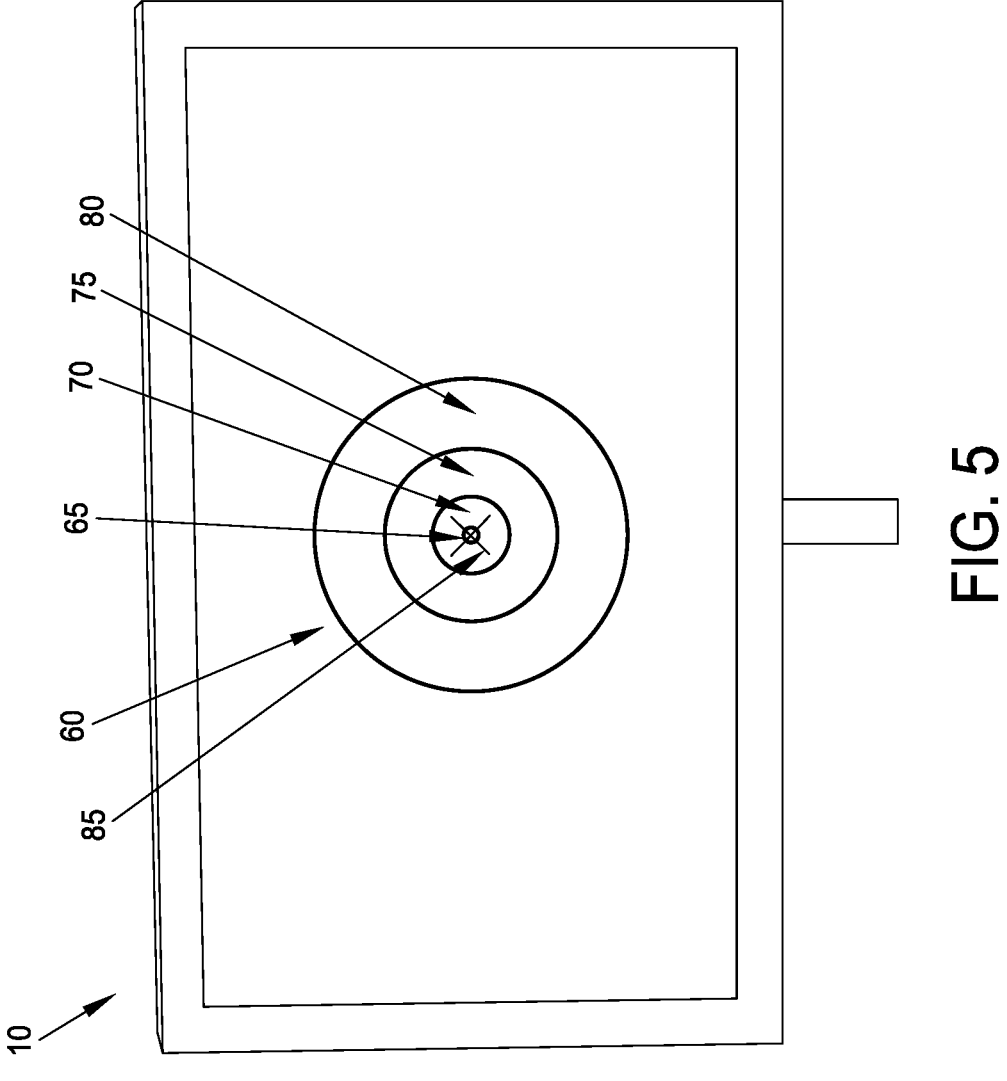

Looking now at FIGS. 4 and 5, FRVES 60 comprises four regions, or rings, i.e., a first ring 65 (for stimulating the fovea region), a second ring 70 (for stimulating the parafovea region), a third ring 75 (for stimulating the perifovea region), and a fourth ring 80 (for stimulating a reference region). In one preferred form of the present invention, rings 65, 70, 75 and 80 of FRVES 60 are related to the subject's field of view according to the following parameters:

| Ring | Radius of outer angle subtense in subject's field of view (in degrees) | Diameter of outer angle subtense in subject's field of view (in degrees) | Segment Area in subject's field of view (in degrees*2) |
|---|---|---|---|
| first ring 65 | 1.5 | 3 | 7 |
| second ring 70 | 4.25 | 8.5 | 50 |
| third ring 75 | 14 | 28 | 559 |
| fourth ring 80 | 25 | 50 | 1,347 |

In use, when it is desired to perform ERG (e.g., mfERG) on a subject, the subject is arrayed (e.g., seated) in front of display 10 such that the subject can view a stimulus displayed on display 10. Right-eye active electrode 35 is attached to the subject so as to make contact with the right eye of the subject, right-eye reference electrode 40 is attached to the subject in a region proximate the right eye of the subject, left-eye active electrode 45 is attached to the subject so as to make contact with the left eye of the subject, left-eye reference electrode 50 is attached to the subject in a region proximate to the left eye of the subject, and ground electrode 55 is attached to the subject in an appropriate area (e.g., the scalp). The free ends of the cluster of electrodes 15 preferably connect to amplifier 20 (see FIG. 2). Display 10 is then used to display FRVES 60 to the eye(s) of the subject. The subject fixates on a fixation point 85 (e.g., a cross, circle, square, etc.) at the center of FRVES 60 (FIG. 3). If desired, fixation point 85 of FREVS 60 may be disposed in more than one of rings 65, 70, 75, 80. By way of example but not limitation, fixation point 85 may span first ring 65 and second ring 70 (see FIG. 5).

Figure 6:
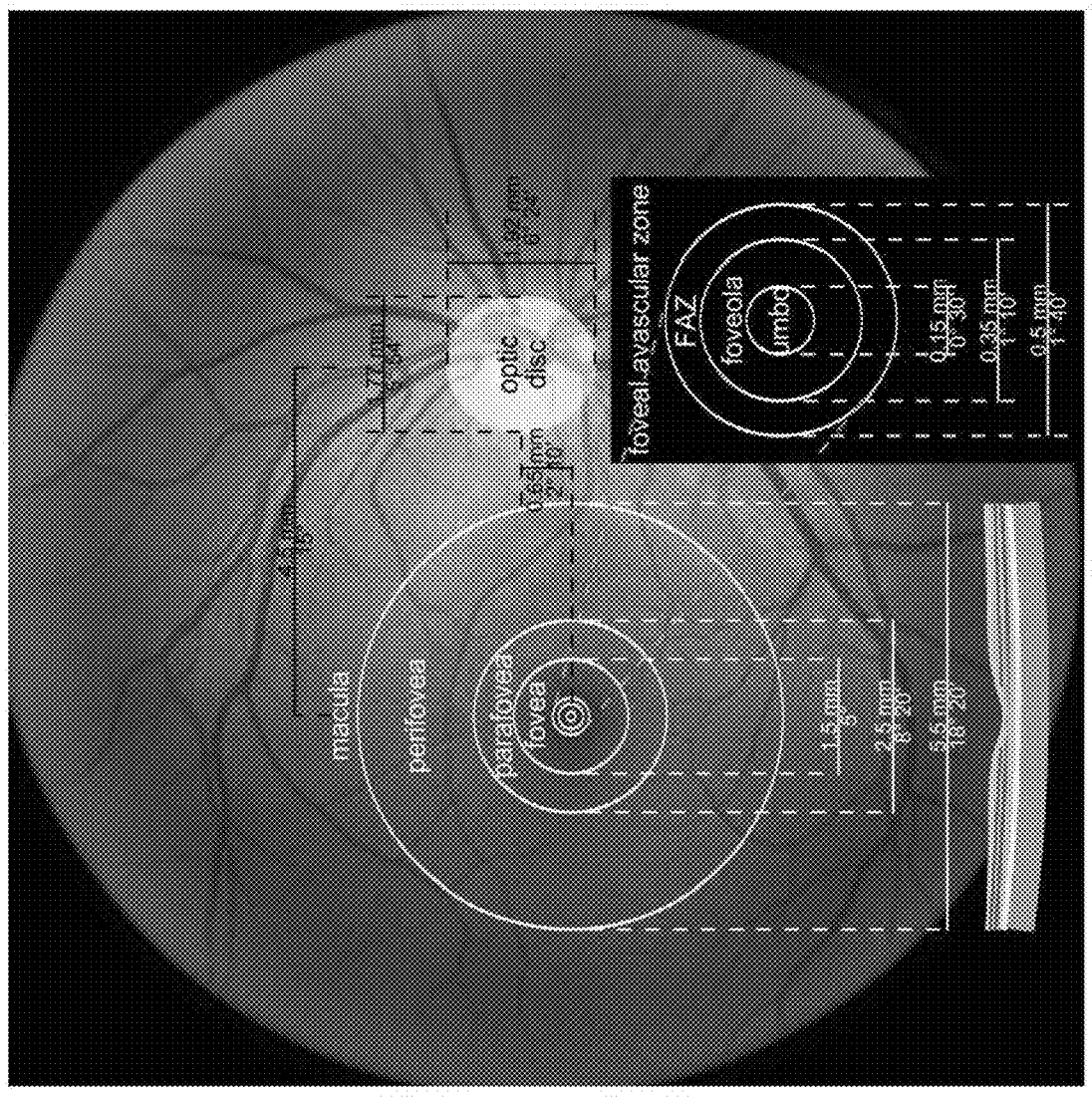
FIG. 6 is a schematic view showing aspects of the anatomy of a retina.

In one preferred form of the present invention, visual electrophysiology system 5 further comprises at least one eye tracking camera (not shown) which may be used to track the direction of gaze of the subject, using that information to either adjust the location of FREVS 60 as it appears on display 10 or, in post-analysis, to make adjustments to correct for the direction of patient gaze. Such adjustments ensure that stimuli provided by second ring 70 and third ring 75 are each optically stimulating the correct portion of the subject's retina in the parafovea and perifovea regions of the subject's macula (see FIG. 6). It should be appreciated that one of the benefits of FRVES 60 is that, because the pattern elements (i.e., rings 65, 70, 75, 80) of FRVES 60 are larger than typical prior art stimuli, FRVES 60 is less sensitive to a subject's eyes moving slightly when performing ERG (e.g., mfERG) (which movement typically happens to at least a slight degree).

In a preferred method of use, rings 65, 70, 75, 80 of FRVES 60 may be run (i.e., projected onto display 10) sequentially to stimulate the appropriate regions of the retina. By way of example but not limitation, multiple flashes of first ring 65 may be displayed on display 10 to stimulate the fovea region, and then multiple flashes of second ring 70 may be displayed on display 10 to stimulate the parafovea region, etc., with the resulting ERG responses each being recorded and separately averaged by amplifier 20, controller 25 and/or computer 30 (see FIG. 2). Alternatively, other flash sequences may be provided to individually stimulate a desired region of the retina, including the so-called m-sequence method that is part of the standard mfERG technique. The standard mfERG technique is well-described in the literature (see, for example, Hood, D C et al., "ISCEV standard for clinical multifocal electroretinography (mfERG)" (2011 edition), Doc. Ophthalmol. (2012) 124:1-13, DOI 10.1007/s10633-011-9296-8).

Figure 1:
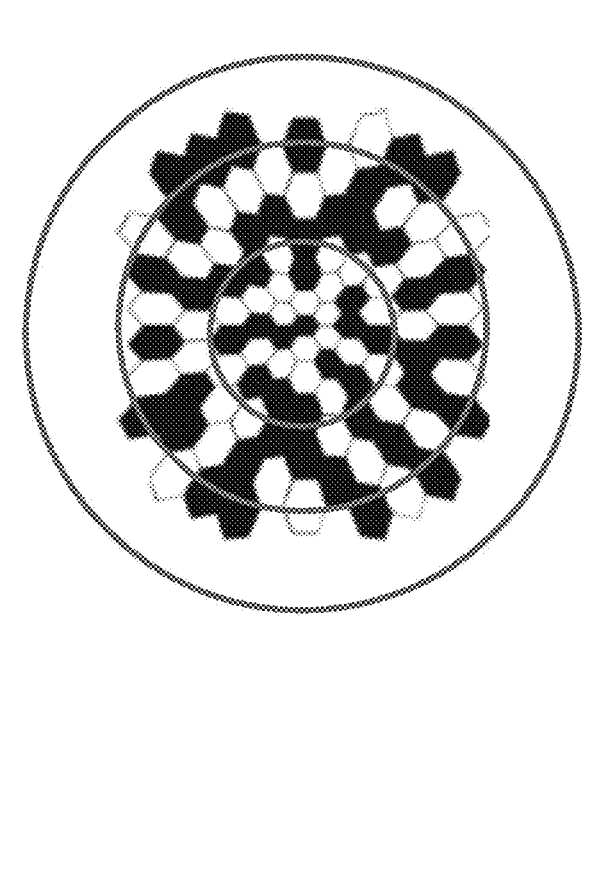
FIG. 1 is a schematic view showing two exemplary prior art stimulus erns.

FRVES 60 is preferably used to stimulate each of the four regions of the retina subtended by the four rings 65, 70, 75, 80 while amplifier 20/controller 25/computer 30 (see FIG. 2) records the electrophysiology response (e.g., the ERG response) in each of the four regions of the subject's eye stimulated by FRVES 60. It will be appreciated that this method of performing ERG (e.g., mfERG) is much faster than prior art systems that rely on prior art stimuli (e.g., the stimuli shown in FIG. 1). By way of example but not limitation, an mfERG test performed using the system of the present invention takes only 30-60 seconds.

It should also be appreciated that, if desired, one or more of rings 65, 70, 75, 80 of FRVES 60 may be divided into one or more sub-rings. By way of example but not limitation, second ring 70 may be divided into two sub-rings 70A, 70B when projected on display 10, whereby to perform an ERG (e.g., an mfERG) using a FRVES 60 that comprises five rings (i.e., first ring 65, second sub-ring 70A, second sub-ring 70B, third ring 75 and fourth ring 80). At the conclusion of such an ERG, the ERG signals recorded from the two sub-rings of second ring 70 (i.e., second sub-ring 70 and second sub-ring 70B) would preferably be combined into a single recording relating to second ring 70, with the result that four ERG recordings would be presented at the end of the ERG. Thus, essentially the same information (i.e., four ERG recordings corresponding to the four regions of the eye stimulated by rings 65, 70, 75 and 80) would be obtained even when one or more of rings 65, 70, 75, 80 are subdivided into sub-rings as would be obtained if the FRVES 60 had been utilized without sub-dividing any of rings 65, 70, 75, 80. Thus it will be appreciated that it is possible to divide one or more of ring 65, 70, 75, 80 into sub-rings, and then combine the recorded signals into a recording corresponding to an ERG recording which would result from performing an ERG (e.g., an mfERG) using FREVS 60 comprising undivided rings 65, 70, 75, 80. It should be appreciated that dividing one ore more of rings 65, 70, 75, 80 into sub-rings would typically increase the amount of time required to perform the ERG, and may decrease the signal-to-noise ratio for the resulting recorded signals of the sub-rings.

If desired, the ERG (e.g., mfERG) performed using the novel system of the present invention produces a test report. Exemplary test reports 90 are shown in FIGS. 7 and 8. In each case, the ERG waveform is recorded and graphed (e.g., on the left side of the test report 90 as shown in FIGS. 7 and 8) and the amplitudes of the ERG response are automatically measured by the system and reported in a table (e.g., on the right side of the test report 90 as shown in FIGS. 7 and 8). In the exemplary test reports 90, the ERG amplitude of the primary response is reported as the "P1", measured in micro-volts per degree squared (uv/deg*2), but other measures such as uVolts may be used as well. Other methods for measuring the retinal responses may also be used, including using just raw amplitude of the response, which is measured in micro-volts. Such methods will be apparent to one of ordinary skill in the art in view of the present disclosure.

Of particular interest in an ERG (e.g., mfERG) performed using FRVES 60, are the amplitudes of the retinal ERG responses to the stimuli provided by second ring 70 and third ring 75. More particularly, it has been discovered that the portion of the retina stimulated by second ring 70 (e.g., the parafovea region) is often the first portion of the retina to be damaged due to drug toxicity in Caucasian human populations. In Asian human populations, retinal damage may first occur in either the portion of the retina stimulated by second ring 70 (e.g., the parafovea region) or the portion of the retina stimulated by third ring 75 (e.g., the perifovea region). If desired, the amplitude of the response from each of the portions of the retina corresponding to stimuli provided by those rings may be compared to (i) prior tests of the subject (e.g., before the person started taking the drug for which retinal toxicity is being monitored), or (ii) average responses of a group of subjects who are not taking a drug that may cause toxicity (e.g., normative data), for each eye tested.

Another important attribute of FRVES 60 is fourth ring 80. Fourth ring 80 stimulates a region of the retina outside of the area where any retinal damage would be expected to occur from drug toxicity. Fourth ring 80 is also located inside the radius that is oftentimes "clipped" in stimulating a subject's retina, e.g., when the subject is wearing glasses or when ophthalmic trial lenses are used to correct the subject's vision to be "best corrected visual acuity" during the test. Fourth ring 80 is designed to stimulate the largest portion of the retina possible that is outside the perifovea region, but inside the field of view that can be "clipped" by lens frames. Thus, fourth ring 80 serves as a healthy retina reference region for the ERG measurement.

Still another important aspect of FRVES 60 is that fourth ring 80 may be used as a reference to the responses to stimuli in second ring 70 and third ring 75. The reason for doing this is that there are a number of factors during the test that can affect the overall amplitude of all regions of the retina that are stimulated, which could lead to an error when comparing test results from one test session to the next. For example, differences in pupil dilation can cause all of the responses to be smaller or larger because of the different levels of light that come from a specified luminance stimulator to the retina, based on differing pupil openings. Also, slight differences in the position of the electrodes 35, 40, 45, 50 from one test to the next will cause all response amplitudes to slightly vary across testing sessions. For this reason, responses to stimuli from fourth ring 80, which stimulates a healthy region of the retina, serve as an important reference for comparison to responses to stimuli from second ring 70 and third ring 75, which stimulate the parafovea region and the perifovea region, respectively (i.e., the regions that may be damaged due to drug toxicity). In the exemplary test reports 90 shown in FIGS. 7 and 8, the second ring 70/fourth ring 80 and third ring 75/fourth ring 80 amplitude ratios are calculated and reported. Each of these ratios are compared either to prior tests of the subject (e.g., before the subject started taking the drug that retinal toxicity is being monitored for) or to average responses of a group of subjects who are not taking a drug that may cause toxicity (e.g., normative data), for each eye tested.

In the foregoing discussion, visual electrophysiology system 5 is generally discussed in the context of performing ERG, and often discussed in the context of performing multifocal electroretinography (mfERG). However, it should be appreciated that visual electrophysiology system 5 may be used to perform substantially any type of electrophysiology test including, but not limited to, multi-focal VEP, Pattern ERG, multi-focal Pattern VEP, Sweep VEP and Pattern VEP.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An ophthalmic electrophysiology system for testing different regions of the retina of a subject for retinal function, said system comprising:
a monitor configured to display:
a first visual electrophysiology stimulus consisting of a single flash of light in the form of a central first ring to stimulate the fovea region of the retina;
a second visual electrophysiology stimulus consisting of a second ring disposed concentrically relative to the central first ring, wherein the second ring is configured to display a single flash of light to stimulate the parafovea region of the retina;
a third visual electrophysiology stimulus consisting of a third ring disposed concentrically relative to the second ring, wherein the third ring is configured to display a single flash of light to stimulate the perifovea region of the retina; and
a fourth visual electrophysiology stimulus consisting of a fourth ring disposed concentrically relative to the third ring, wherein the fourth ring is configured to display a single flash of light to stimulate a reference region of the retina;
at least one active electrode;
at least one reference electrode; and
a computer configured to:
control said monitor to display each of the single flashes of light sequentially in order to stimulate the corresponding region of the retina; and
receive electrical signals from said at least one active electrode and said at least one reference electrode, and process the electrical signals.

2. The system according to claim 1 wherein at least one of the first visual electrophysiology stimulus, the second visual electrophysiology stimulus, the third visual electrophysiology stimulus and the fourth visual electrophysiology stimulus is flashed on the monitor multiple times.

3. The system according to claim 1 wherein said monitor is a liquid crystal display (LCD).

4. The system according to claim 1 wherein the at least one active electrode is configured to contact the eye of the subject, and the at least one reference electrode is configured to contact the subject proximate to the eye of the subject.

5. The system according to claim 1 further comprising at least one ground electrode configured to contact the subject.

6. The system according to claim 1 wherein the system comprises a first active electrode for contacting a first eye of the subject, a first reference electrode for contacting the subject proximate to the first eye of the subject, a second active electrode for contacting a second eye of the subject, and a second reference electrode for contacting the subject proximate to the second eye of the subject.

7. The system according to claim 1 wherein the system further comprises an amplifier, and further wherein said at least one active electrode and said at least one reference electrode are electrically connected to said amplifier;
wherein said amplifier is configured to amplify the electrical signals from said at least one active electrode and said at least one reference electrode.

8. The system according to claim 1 further comprising a controller configured to control said monitor.

9. The system according to claim 1 wherein the test to be performed on the subject is multifocal electroretinography (mfERG).

10. The system according to claim 1 wherein said computer is configured to process the electrical signals into a test report.

11. The system according to claim 1 wherein said computer is configured to process the electrical signals to calculate a voltage potential from the retina of the subject, whereby to determine retinal function of the subject.

12. The system according to claim 1 wherein at least one of the second ring, the third ring and the fourth ring comprises at least two sub-rings.

13. The system according to claim 12 wherein the at least two sub-rings are displayed independently to the subject, and further wherein the electrical signals from the stimulus provided by the at least two sub-rings are combined to create a recording equivalent to the electrical signals provided by a single ring of the visual electrophysiology stimulus.

14. The system according to claim 1 wherein (i) when the monitor displays the first visual electrophysiology stimulus to the subject, the second visual electrophysiology stimulus is not displayed, (ii) when the monitor displays the second visual electrophysiology stimulus to the subject, the first visual electrophysiology stimulus and the third visual electrophysiology stimulus are not displayed, (iii) when the monitor displays the third visual electrophysiology stimulus to the subject, the second visual electrophysiology stimulus and the fourth visual electrophysiology stimulus are not displayed, and (iv) when the monitor displays the fourth visual electrophysiology stimulus to the subject, the third visual electrophysiology stimulus is not displayed.

15. A method for testing different regions of the retina of a subject for retinal function, said method comprising:
providing a system comprising:
a monitor configured to display:
a first visual electrophysiology stimulus consisting of a single flash of light in the form of a central first ring to stimulate the fovea region of the retina;
a second visual electrophysiology stimulus consisting of a second ring disposed concentrically relative to the central first ring, wherein the second ring is configured to display a single flash of light to stimulate the parafovea region of the retina;
a third visual electrophysiology stimulus consisting of a third ring disposed concentrically relative to the second ring, wherein the third ring is configured to display a single flash of light to stimulate the perifovea region of the retina; and
a fourth visual electrophysiology stimulus consisting of a fourth ring disposed concentrically relative to the third ring, wherein the fourth ring is configured to display a single flash of light to stimulate a reference region of the retina;
at least one active electrode;

at least one reference electrode; and a computer configured to:

control said monitor to display each of the single flashes of light sequentially in order to stimulate the corresponding region of the retina; and receive electrical signals from said at least one active electrode and said at least one reference electrode, and process the electrical signals;

attaching said at least one active electrode to the subject;

attaching said at least one reference electrode to the subject;

using said computer to (i) control said monitor to display each of the single flashes of light sequentially in order to stimulate the corresponding region of the retina, (ii) receive electrical signals from said at least one active electrode and said at least one reference electrode, and process the electrical signals, and (iii) calculate an amplitude of at least one of the electrical signals evoked from the displayed visual electrophysiology stimulus; and using said computer to compare the amplitude of the at least one electrical signal evoked from each displayed visual electrophysiology stimulus to previously-determined amplitude data, and calculating a ratio between (i) the amplitude of the at least one electrical signal evoked from each displayed visual electrophysiology stimulus, and (ii) the previously-determined amplitude data.

16. The method according to claim 15 wherein at least one of the first visual electrophysiology stimulus, the second visual electrophysiology stimulus, the third visual electrophysiology stimulus and the fourth visual electrophysiology stimulus is flashed on the monitor multiple times.

17. The method according to claim 15 wherein said at least one active electrode is attached to an eye of the subject, and said at least one reference electrode is attached to the subject proximate to the eye of the subject.

18. The method according to claim 15 further comprising attaching a ground electrode to the subject.

19. The method according to claim 15 wherein the system comprises a first active electrode for contacting a first eye of the subject, a first reference electrode for contacting the subject proximate to the first eye of the subject, a second active electrode for contacting a second eye of the subject, and a second reference electrode for contacting the subject proximate to the second eye of the subject.

20. The method according to claim 15 wherein the system further comprises an amplifier, and further wherein said at least one active electrode and said at least one reference electrode are electrically connected to said amplifier;

wherein said amplifier is configured to amplify the electrical signals from said at least one active electrode and said at least one reference electrode.

21. The method according to claim 15 wherein the system further comprises a controller configured to control said monitor.

22. The method according to claim 15 wherein the test to be performed on the subject is multifocal electroretinography (mfERG).

23. The method according to claim 15 wherein the computer is configured to process the electrical signals into a test report.

24. The method according to claim 23 wherein said test report is compared against normative data for the subject to determine whether there is any retinal damage to the eye of the subject.

25. The method according to claim 15 wherein data received by either said at least one active electrode or said at least one reference electrode when said fourth visual electrophysiology stimulus is used to stimulate the reference region of the retina is used as a reference against which to compare data received by either said at least one active electrode or said at least one reference electrode when at least one of said first visual electrophysiology stimulus, said second visual electrophysiology stimulus and said third visual electrophysiology stimulus stimulate the retina.

26. The method according to claim 15 wherein the eye of the subject is stimulated for the purpose of monitoring retinal toxicity.

27. The method according to claim 15 wherein the computer is configured to process the electrical signals to calculate a voltage potential from the retina of the subject, whereby to determine retinal function of the subject.

28. The method according to claim 15 wherein at least one of the second ring, the third ring and the fourth ring comprises at least two sub-rings.

29. The method according to claim 28 wherein the at least two sub-rings are displayed independently to the subject, and further wherein the electrical signals from the stimulus provided by the at least two sub-rings are combined to create a recording equivalent to the electrical signals provided by a single ring of the visual electrophysiology stimulus.

30. The method according to claim 15 wherein the amplitude of the electrical signal evoked from displaying the second visual electrophysiology stimulus is compared to previously-determined amplitude data relating to the parafovea region of the retina.

31. The method according to claim 15 wherein the amplitude of the electrical signal evoked from displaying the third visual electrophysiology stimulus is compared to previously-determined amplitude data relating to the perifovea region of the retina.

32. The method according to claim 15 wherein (i) when the monitor displays the first visual electrophysiology stimulus to the subject, the second visual electrophysiology stimulus is not displayed, (ii) when the monitor displays the second visual electrophysiology stimulus to the subject, the first visual electrophysiology stimulus and the third visual electrophysiology stimulus are not displayed, (iii) when the monitor displays the third visual electrophysiology stimulus to the subject, the second visual electrophysiology stimulus and the fourth visual electrophysiology stimulus are not displayed, and (iv) when the monitor displays the fourth visual electrophysiology stimulus to the subject, the third visual electrophysiology stimulus is not displayed.

* * * * *